United States Patent
Fujii et al.

(10) Patent No.: US 6,521,627 B1
(45) Date of Patent: Feb. 18, 2003

(54) 5-IODO-4-PHENETHYLAMINOPYRIMIDINE DERIVATIVE, INTERMEDIATE THEREOF, PROCESSES FOR PRODUCING THE SAME AND AGRICULTURAL AND HORTICULTURAL PESTICIDES

(75) Inventors: Katsutoshi Fujii, Ube (JP); Yoshinori Yamanaka, Ube (JP); Kiyoshi Tsutsumiuchi, Ube (JP); Youichi Yoshida, Ube (JP)

(73) Assignee: UBE Industries, Ltd., Yamaguchi (JP)

( * ) Notice: Subject to any disclaimer, the term of this patent is extended or adjusted under 35 U.S.C. 154(b) by 0 days.

(21) Appl. No.: 09/673,494
(22) PCT Filed: Apr. 8, 1999
(86) PCT No.: PCT/JP99/01855
§ 371 (c)(1),
(2), (4) Date: Oct. 16, 2000
(87) PCT Pub. No.: WO99/52880
PCT Pub. Date: Oct. 21, 1999

(30) Foreign Application Priority Data

Apr. 14, 1998 (JP) .............................. 10-102414
Apr. 17, 1998 (JP) .............................. 10-107731

(51) Int. Cl.$^7$ .................. C07D 239/42; A01N 43/54
(52) U.S. Cl. ..................... 514/256; 544/326
(58) Field of Search .................. 544/334, 326; 514/256

(56) References Cited

U.S. PATENT DOCUMENTS 4,977,264 A  12/1990  Mills et al. ................ 544/334
5,498,612 A  3/1996  Obata et al. ................ 514/256

FOREIGN PATENT DOCUMENTS

EP  0470600  2/1992
EP  0665225  8/1995

Primary Examiner—John M. Ford
(74) Attorney, Agent, or Firm—Jordan and Hamburg

(57) ABSTRACT

The present invention is to provide a novel 5-iodo-4-phenethylaminopyrimidine derivative represented by the following formula (1):

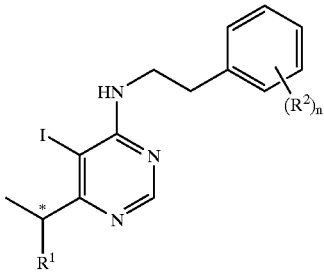

(1)

wherein $R^1$ represents a halogen atom, a $C_{2-4}$ acyloxy group or a hydroxyl group; $R^2$ represents a hydrogen atom, a halogen atom, a $C_{1-4}$ alkyl group, a $C_{1-4}$ haloalkyl group, a $C_{1-4}$ alkoxy group or a $C_{1-4}$ haloalkoxy group; n is an integer of 1 to 3; and * represents an asymmetric carbon atom, useful as pesticides, a synthetic intermediate thereof and processes for producing these compounds, and pesticides containing the 5-iodo-4-phenethylaminopyrimidine derivative(s).

9 Claims, No Drawings

5-IODO-4-PHENETHYLAMINOPYRIMIDINE DERIVATIVE, INTERMEDIATE THEREOF, PROCESSES FOR PRODUCING THE SAME AND AGRICULTURAL AND HORTICULTURAL PESTICIDES

This is a U.S. National Stage under 35 U.S.C. 371 of PCT /JP 99/01855 application, filed Apr. 8, 1999.

BACKGROUND OF THE INVENTION

This invention relates to a novel 5-iodo-4-phenethylaminopyrimidine derivative useful as agricultural and horticultural pesticides, a novel 4-chloro-5-iodo-6-(α-substituted ethyl)pyrimidine which is a preparation intermediate thereof, processes for producing these compounds and agricultural and horticultural pesticides.

PRIOR ART

Some 4,5-dihalogeno-6-(α-substituted ethyl)pyrimidines useful as an intermediate for medicines or agricultural chemicals have been known (for example, Japanese Provisional Patent Publication No. 320141/1993, etc.). However, 4-chloro-5-iodo-6-(α-substituted ethyl)pyrimidine in which the 5-position of the pyrimidine ring is substituted by an iodine atom as in the present invention has not yet been disclosed.

Moreover, as a 4-phenethylaminopyrimidine derivative which is similar to the present invention, there is Japanese Provisional Patent PublicationNo. 258223/1995. However, the 4-phenethylaminopyrimidine derivative in which the 5-position of the pyrimidine ring is substituted by an iodine atom has not been disclosed.

Accordingly, the 5-iodo-4-phenethylaminopyrimidine derivative of the present invention would be a novel compound is a novel compound and it has been not known to have agricultural and horticultural pesticidal activities.

An object of the present invention is to provide a novel 5-iodo-4-phenethylaminopyrimidine derivative, its process for producing the same, and an agricultural and horticultural pesticide containing the same as an effective ingredient.

Another object of the present invention is to provide a novel 4-chloro-5-iodo-6-(α-substituted ethyl)pyrimidine which is useful as an intermediate for medicines and agricultural chemicals.

SUMMARY OF THE INVENTION

The present inventors have studied to solve the above-mentioned problems, and as a result, they have found that a novel 5-iodo-4-phenethylaminopyrimidine has remarkable agricultural and horticultural insecticidal, acaricidal, nematocidal and fungicidal activities whereby they have accomplished the present invention.

Also, the present inventors have also studied to solve the above-mentioned problems, and as a result, they have found a process for producing a novel 4-chloro-5-iodo-6-(α-substituted ethyl)pyrimidine, whereby they have accomplished the present invention.

That is, the present invention is as mentioned below.

The first invention relates to a 5-iodo-4-phenethylaminopyrimidine derivative represented by the following formula (1):

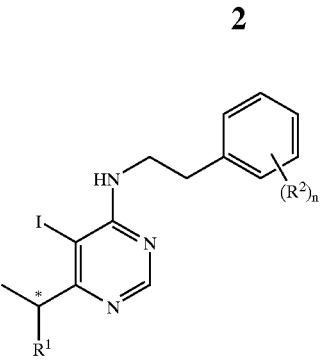

(1)

wherein $R^1$ represents a halogen atom, an acyloxy group having 2 to 4 carbon atoms or a hydroxyl group; $R^2$ represents a hydrogen atom, a halogen atom, an alkyl group having 1 to 4 carbon atoms, a haloalkyl group having 1 to 4 carbon atoms, an alkoxy group having 1 to 4 carbon atoms, or a haloalkoxy group having 1 to 4 carbon atoms;

n is an integer of 1 to 3; and * represents an asymmetric carbon atom.

The second invention relates to a process for producing the 5-iodo-4-phenethylaminopyrimidine derivative represented by the above-mentioned formula (1) which comprises allowing a pyrimidine represented by the following formula (2):

(2)

wherein $R^1$ and * have the same meanings as defined above, to react with a phenethylamine represented by the following formula (3):

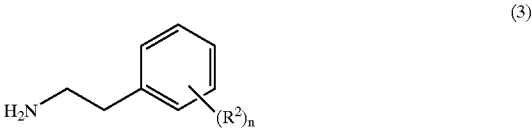

(3)

wherein $R^2$ and n have the same meanings as defined above.

The third invention relates to a 4-chloro-5-iodo-6-(α-substituted ethyl)pyrimidine represented by the following formula (2):

(2)

wherein $R^1$ and * have the same meanings as defined above.

The fourth invention relates to a process for producing 4-chloro-5-iodo-6-(α-substituted ethyl)pyrimidine represented by the following formula (2-1):

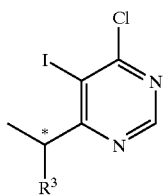
(2-1)

wherein R³ represents a chlorine atom or a bromine atom and * has the same meaning as defined above, which comprises allowing a pyrimidine represented by the following formula (4):

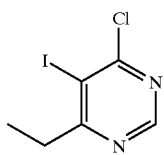
(4)

to react with a halogen represented by the following formula (5):

(R³)₂      (5)

wherein R³ has the same meaning as defined above.

The fifth invention relates to a process for producing a 4-chloro-5-iodo-6-(α-substituted ethyl)pyrimidine represented by the following formula (2-2):

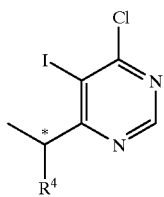
(2-2)

wherein R⁴ represents an acyloxy group having 2 to 4 carbon atoms, and * has the same meaning as defined above, which comprises allowing the pyrimidine represented by the following formula (2-1):

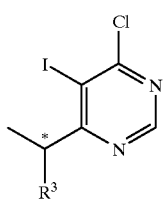
(2-1)

wherein R³ and * have the same meanings as defined above, to react with a lower aliphatic acid represented by the following formula (6):

R⁴—H      (6)

wherein R⁴ has the same meaning as defined above.

The sixth invention relates to a process for producing a 4-chloro-5-iodo-6-(α-substituted ethyl)pyrimidine represented

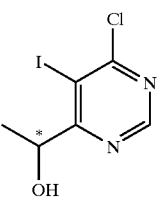
(2-3)

by the following formula (2-3):

wherein * has the same meaning as defined above, which comprises allowing the pyrimidine represented by the following formula (2-2):

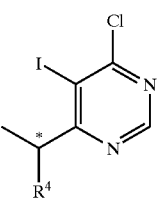
(2-2)

wherein R⁴ and * have the same meanings as defined above, to react with an inorganic base represented by the following formula (7):

M—OH      (7)

wherein M represents an alkali metal.

The seventh invention relates to a process for producing a 4-chloro-5-iodo-6-(α-substituted ethyl)pyrimidine represented by the following formula (2-4):

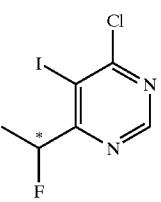
(2-4)

wherein * has the same meaning as defined above, which comprises allowing the pyrimidine represented by the following formula (2-3):

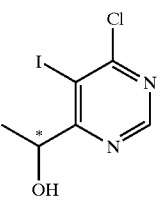
(2-3)

wherein * has the same meaning as defined above, to react with a fluorinating agent represented by the following formula (8):

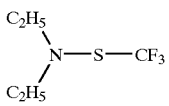

(8)

The eighth invention relates to agricultural and horticultural pesticides containing the 5-iodo-4-phenethylaminopyrimidine represented by the above-mentioned formula (1) as an effective ingredient.

DETAILED DESCRIPTION OF THE INVENTION

In the following, the present invention is explained in detail.

Various kinds of the substituents mentioned in the above respective compounds are as follows.

($R^1$)

$R^1$ represents a halogen atom, an acyloxy group having 2 to 4 carbon atoms or a hydroxyl group.

As the halogen atom, there may be mentioned a chlorine atom, an iodine atom, a bromine atom, a fluorine atom, etc.; and preferably a chlorine atom and a fluorine atom.

As the acyloxy group having 2 to 4 carbon atom, there may be mentioned those having a straight or branched alkyl group; preferably an acetyloxy group.

($R^2$)

$R^2$ represents a hydrogen atom, a halogen atom, an alkyl group having 1 to 4 carbon atoms, a haloalkyl group having 1 to 4 carbon atoms, an alkoxy group having 1 to 4 carbon atoms, or a haloalkoxy group having 1 to 4 carbon atoms.

As the halogen atom in $R^2$, there may be mentioned a chlorine atom, an iodine atom, a bromine atom, a fluorine atom, etc.; and preferably a chlorine atom and a fluorine atom.

As the alkyl group having 1 to 4 carbon atoms, there may be mentioned a straight or branched alkyl group; and preferably a methyl group.

As the haloalkyl group having 1 to 4 carbon atoms, there may be mentioned a trifluoromethyl group, a 2,2,2-trifluoroethyl group, a 2-fluoroethyl group, etc., and preferably a trifluoromethyl group.

As the alkoxy group having 1 to 4 carbon atoms, there may be mentioned a straight or branched one, and preferably a methoxy group.

As the haloalkoxy group having 1 to 4 carbon atoms, there may be mentioned a difluoromethoxy group, a trifluoromethoxy group, a 2,2,2-trifluoroethoxy group, a 2-fluoroethoxy group, etc., and more preferably a trifluoromethoxy group and a 2,2,2-trifluoroethoxy group.

(n)

n is an integer of 1 to 3; and preferably 1 or 2.

The compounds (1) of the present invention have an amino group so that an acid addition salt derived therefrom is also included in the present invention.

As an acid which forms an acid addition salt, there may be mentioned, for example, an inorganic acid such as hydrochloric acid, hydrobromic acid, nitric acid, sulfuric acid, phosphoric acid, etc.; a carboxylic acid such as formic acid, oxalic acid, fumaric acid, adipic acid, stearic acid, oleic acid, aconitic acid, etc.; a sulfonic acid such as methane-sulfonic acid, benzenesulfonic acid, p-toluenesulfonic acid, etc.; saccharine, etc.

Also, the compounds (1) or (2) of the present invention contain asymmetric carbon atom represented by * so that the respective optical isomers, racemic isomers or mixture thereof derived therefrom are each included in the present invention.

As the compounds (1), those in which the above-mentioned various substituents are combined may be mentioned, and those preferred in view of chemical effects are as follows.

(1) Compound (1) in which $R^1$ is a halogen atom and $R^2$ is a hydrogen atom.

(2) Compound (1) in which $R^1$ and $R^2$ are halogen atoms and n is 1.

(3) Compound (1) in which $R^1$ is an acyloxy group having 2 to 4 carbon atoms and $R^2$ is a hydrogen atom.

(4) Compound (1) in which $R^1$ is a halogen atom, $R^2$ is an alkyl group having 1 to 4 carbon atoms and n is 1.

(5) Compound (1) in which $R^1$ is a halogen atom, $R^2$ is an alkoxy group having 1 to 4 carbon atoms and n is 1.

(6) Compound (1) in which $R^1$ is a halogen atom, $R^2$ is a haloalkoxy group having 1 to 4 carbon atoms and n is 1.

Also, as the compound (2) which is a synthetic intermediate of the above-mentioned compound (1), those having the substituent preferred as $R^1$ mentioned above may be mentioned.

(Synthetic method of Compound (1))

As a preferred process for producing the 5-iodo-4-phenethylaminopyrimidine derivative represented by the above-mentioned formula (1), there may be mentioned, in addition to Synthetic method 1 described as the second invention, the following four kinds of production processes (Synthetic methods 2 to 5).

(Synthetic method 2)

A process for producing a 5-iodo-4-phenethylaminopyrimidine derivative (referred to as Compound (1-2)) represented by the following formula (1-2):

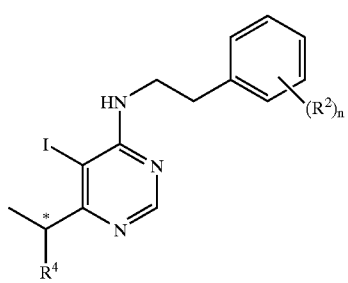

(1-2)

wherein $R^2$, n and * have the same meanings as defined above and $R^4$ represents a lower acyloxy group, which comprises allowing a 4-phenethylaminopyrimidine derivative (referred to as Compound (1-1)) represented by the following formula (1-1):

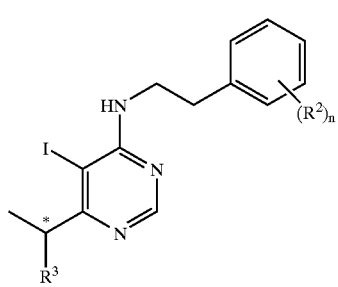

(1-1)

wherein $R^2$, n and * have the same meanings as defined above and $R^3$ represents a chlorine atom or a bromine atom, to react with a lower aliphatic carboxylic acid represented by the following formula (6):

R⁴—H  (6)

wherein R⁴ has the same meaning as defined above.

(Synthetic method 3)

A process for producing a 5-iodo-4-phenethylaminopyrimidine derivative (referred to as Compound (1-3)) represented by the following formula (1-3):

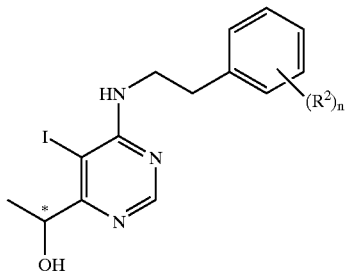

(1-3)

wherein R², n and * have the same meanings as defined above, which comprises allowing the 4-phenethylaminopyrimidine derivative (referred to as Compound (1-2)) represented by the above formula (1-2) to react with an inorganic base represented by the following formula (7):

M—OH  (7)

wherein M represents an alkali metal.

(Synthetic method 4)

A process for producing a 5-iodo-4-phenethylaminopyrimidine derivative (referred to as Compound (1-4)) represented by the following formula (1-4):

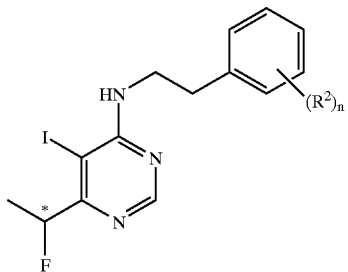

(1-4)

wherein R², n and * have the same meanings as defined above, which comprises allowing the 4-phenethylaminopyrimidine derivative (referred to as Compound (1-3)) represented by the above formula (1-3) to react with a fluorinating agent (diethylaminosulfur trifluoride: DAST) represented by the following formula (8):

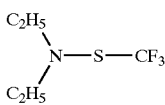

(8)

(Synthetic method 5)

A process for producing the 5-iodo-4-phenethylaminopyrimidine derivative (referred to as Compound (1-4)) represented by the above formula (1-4), which comprises allowing the 4-phenethylaminopyrimidine derivative (referred to as Compound (1-1)) represented by the following formula (1-1):

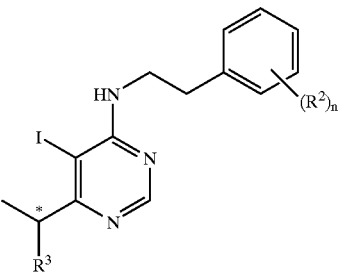

(1-1)

wherein R², R³, n and * have the same meanings as defined above, to react with a compound represented by the following formula (9):

M—F  (9)

wherein M has the same meaning as defined above.

The above-mentioned Synthetic methods 1 to 5 of the compounds (1) according to the present invention are described in more detail.

(Synthetic method 1)

Synthetic method 1 is a method in which Compound (2) and Compound (3) are reacted in a solvent in the presence of a base to obtain Compound (1).

As a kind of the solvent, it is not particularly limited so long as it does not directly participate in the present reaction, and there may be mentioned, for example, a chlorinated or not chlorinated aromatic, aliphatic or alicyclic hydrocarbon such as benzene, toluene, xylene, methylnaphthalene, petroleum ether, ligroin, hexane, chlorobenzene, dichlorobenzene, chloroform, dichloroethane, trichloroethylene, etc.; an ether such as tetrahydrofuran, dioxane, diethyl ether, etc.; a nitrile such as acetonitrile, propionitrile, etc.; a ketone such as acetone, methyl ethyl ketone, etc.; an aprotic polar solvent such as N,N-dimethylformamide, dimethylsulfoxide, sulforane, N,N-dimethylimidazolidinone, N-methylpyrrolidone, etc.; and a mixture of the above-mentioned solvents.

With regard to an amount of the solvent, it may be used so that Compound (2) becomes 5 to 80% by weight; and preferably 10 to 70% by weight.

As a kind of the base, it is not specifically limited, and there may be mentioned organic and inorganic bases, for example, a tertiary amine such as triethylamine, an organic base such as DBU, an inorganic base such as a hydride, hydroxide, carbonate, hydrogen carbonate of an alkali metal and alkaline earth metal; and preferably an organic base such as triethylamine.

An amount of the base to be used is 1 to 5-fold mole based on Compound (2); preferably 1.2 to 2.0-fold mole.

A reaction temperature is not specifically limited, and it is within the temperature range from a room temperature to a boiling point or less of the solvent to be used; preferably 60 to 110° C.

A reaction time may vary depending on the above-mentioned concentration and temperature; and generally 0.5 to 5 hours.

An amount of the starting compounds to be used is 1.0 to 5-fold mol of Compound (3) based on the amount of Compound (2); and 1 to 1.1-fold mol is preferred.

Compound (2) to be used in the present invention can be prepared by the method shown in the following scheme.

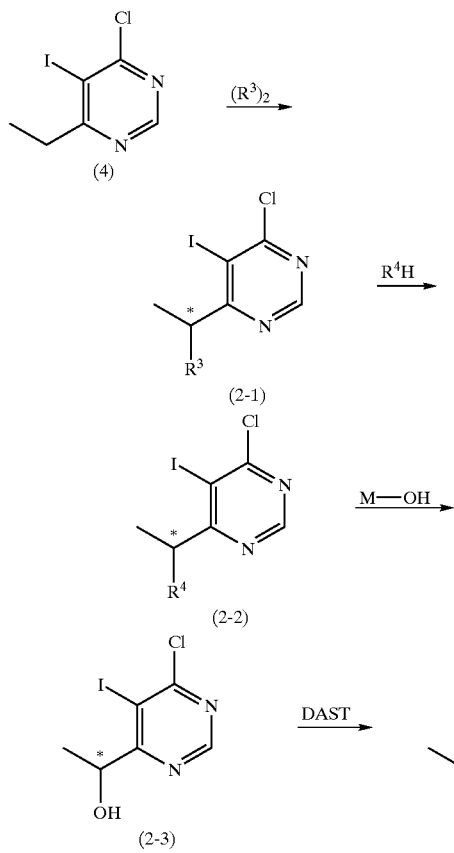

wherein $R^3$, $R^4$, M and * have the same meanings as defined above; and DAST represents diethylaminosulfur trifluoride.

Compound (4) can be produced by the method shown in the following scheme according to the method described in, for example, Journal of Chemical Society (JCS) pp. 3478–3481 (1955).

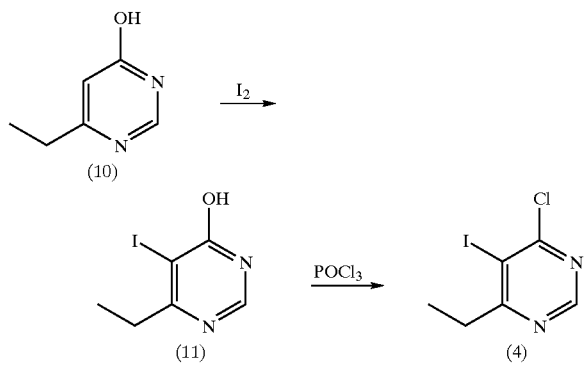

With regard to the synthesis of Compound (2-4) from Compound (4), it is described in detail below (Synthetic methods 6 to 9).

As Compound (3), a commercially available product may be used or it may be produced according to the method shown below.

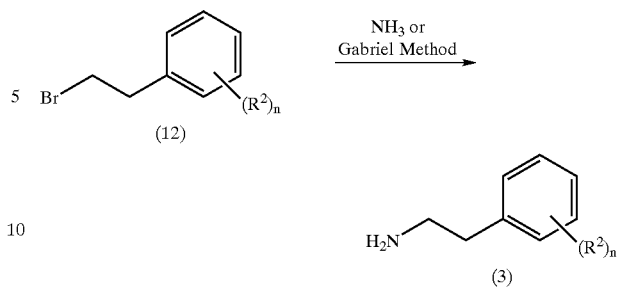

wherein $R^2$ and n have the same meanings as defined above.

The desired compound (1) produced as mentioned above may be subjected to usual post-treatment such as extraction, concentration, filtration, etc., after the reaction, and, if necessary, may be subjected to purification by the known methods such as recrystallization, various kinds of chromatographies, etc.

(Synthetic method 2)

Synthetic method 2 is a method of obtaining Compound (1-2) (a compound in which $R^1$ in the compound (1) is an acyloxy group having 2 to 4 carbon atoms) by reacting Compound (1-1) and Compound (4) in a solvent.

As a kind of the solvent, there may be mentioned an ether, a ketone as described in Synthetic method 1, an amide such as N,N-dimethylacetamide; 1,3-dimethyl-2-imidazolidone, sulforane, dimethylsulfoxide; and a mixture of the above-mentioned solvents; and preferably N,N-dimethylformamide of amides.

An amount of the solvent may be set in such an amount that Compound (1-1) becomes 5 to 80% by weight; preferably 10 to 70% by weight.

As a kind of a base, there may be mentioned an inorganic base mentioned in Synthetic method 1; preferably potassium carbonate.

An amount of the base to be used is 1 to 5-fold mol based on the amount of Compound (1-1), preferably 2 to 5-fold mol.

A reaction temperature is not specifically limited, and is within the temperature range of room temperature to a boiling point of the solvent to be used or less; preferably 60 to 100° C.

A reaction time may vary depending on the above-mentioned concentration and temperature; and generally 0.5 to 8 hours.

As Compound (4), a commercially available product may be used.

The desired Compound (1-2) prepared as mentioned above may be subjected to usual post-treatment such as extraction, concentration, filtration, etc., after the reaction, and, if necessary, may be subjected to purification by the known methods such as recrystallization, various kinds of chromatographies, etc.

(Synthetic method 3)

Synthetic method 3 is a method of obtaining Compound (1-3) by reacting Compound (1-2) and Compound (5) in a solvent.

As a kind of the solvent, there may be mentioned an ether, a ketone, an amide as described in Synthetic method 1; an alcohol (methanol, ethanol, propanol, butanol, etc.); water; and a mixture of the above-mentioned solvents; and preferably a mixture of an alcohol (methanol, ethanol) and water.

An amount of the solvent may be set in such an amount that Compound (1-2) becomes 5 to 80% by weight; preferably 10 to 70% by weight.

As Compound (5), there may be mentioned inorganic bases mentioned in Synthetic method 1 which are commercially available products; preferably sodium hydroxide and potassium hydroxide.

An amount of the base to be used is 1 to 2-fold mol based on the amount of Compound (1-2), preferably 1 to 1.5-fold mol.

A reaction temperature is within the temperature range of 0° C. to room temperature; preferably room temperature.

A reaction time may vary depending on the above-mentioned concentration and temperature; and generally 0.5 to 3 hours.

The desired Compound (1-3) prepared as mentioned above may be subjected to usual post-treatment such as extraction, concentration, filtration, etc., after the reaction, and, if necessary, may be subjected to purification by the known methods such as recrystallization, various kinds of chromatographies, etc.

(Synthetic method 4)

Synthetic method 4 is a method of obtaining Compound (1-4) by reacting Compound (1-3) and Compound (6) in a solvent or without solvent.

As a kind of the solvent, there may be mentioned a chlorinated or not chlorinated aromatic, aliphatic or alicyclic hydrocarbon or an ether as described in Synthetic method 1; and preferably a chlorinated aliphatic hydrocarbon such as dichloromethane.

An amount of the solvent may be set in such an amount that Compound (1-3) becomes 5 to 80% by weight; preferably 10 to 70% by weight.

A reaction temperature is not specifically limited, and is within the temperature range of room temperature to a boiling point or less of the solvent to be used; preferably 0° C. to room temperature.

A reaction time may vary depending on the above-mentioned concentration and temperature; and generally 0.5 to 3 hours.

As Compound (6), it is not specifically limited; and the above-mentioned diethylaminosulfur trifluoride (DAST) which is a commercially available product is preferred.

An amount of Compound (6) to be used is 1 to 2-fold mol based on the amount of Compound (1-3), preferably 1 to 1.5-fold mol.

The desired Compound (1-4) prepared as mentioned above may be subjected to usual post-treatment such as extraction, concentration, filtration, etc., after the reaction, and, if necessary, may be subjected to purification by the known methods such as recrystallization, various kinds of chromatographies, etc.

(Synthetic method 5)

Synthetic method 5 is a method of obtaining Compound (1-4) by reacting Compound (1-1) and Compound (7) in a solvent.

As a kind of the solvent, there may be mentioned an amide such as N,N-dimethylformamide, N,N-dimethylacetamide; 1,3-dimethyl-2-imidazolidone, sulforane, dimethylsulfoxide; and a mixture of the above-mentioned solvents.

An amount of the solvent may be set in such an amount that Compound (1-4) becomes 5 to 80% by weight; preferably 10 to 70% by weight.

A reaction temperature is within the temperature range of room temperature to a boiling point or less of the solvent to be used; preferably 100 to 120° C.

A reaction time may vary depending on the above-mentioned concentration and temperature; and generally 1 to 15 hours.

As Compound (7), there may be mentioned potassium fluoride, sodium fluoride, cesium fluoride which are commercially available products; preferably potassium fluoride and cesium fluoride.

An amount of Compound (7) to be used is 1 to 5-fold mol based on the amount of Compound (1-1), preferably 1 to 3-fold mol.

The desired Compound (1-4) prepared as mentioned above may be subjected to usual post-treatment such as extraction, concentration, filtration, etc., after the reaction, and, if necessary, may be subjected to purification by the known methods such as recrystallization, various kinds of chromatographies, etc.

Next, a method for preparing 4-chloro-5-iodo-6-(α-substituted ethyl)pyrimidine which is a synthetic intermediate of the present invention is explained below.

(Synthetic method 6)

Synthetic method 6 is a method of obtaining Compound (2-1) by reacting Compound (4) and Compound (5) in a solvent.

As a kind of the solvent, it is not specifically limited so long as it does not directly participate in the present reaction, and there may be mentioned, for example, a chlorinated or not chlorinated aromatic, aliphatic or alicyclic hydrocarbon such as benzene, toluene, xylene, methylnaphthalene, petroleum ether, ligroin, hexane, chlorobenzene, dichlorobenzene, chloroform, dichloromethane, dichloroethane, trichloroethylene, etc.; an ether such as tetrahydrofuran, dioxane, diethyl ether, etc.; and a mixture of the above-mentioned solvents; and preferably a chlorinated aliphatic hydrocarbon such as chloroform, dichloromethane and dichloroethane.

An amount of the solvent may be set in such an amount that Compound (4) becomes 5 to 80% by weight; preferably 10 to 70% by weight.

A reaction temperature is not particularly limited and is within the temperature range of room temperature to a boiling point or less of the solvent to be used; preferably 10 to 30° C.

A reaction time may vary depending on the above-mentioned concentration and temperature; and generally 0.5 to 5 hours.

Amounts of the starting materials to be used are 1.0 to 5-fold mol of Compound (5) based on the amount of Compound (4), preferably 1 to 1.3-fold mol.

Compound (4) to be used in the present invention can be produced, as mentioned above, by the method described in, for example, Journal of Chemical Society (JCS), pp. 3478–3481 (1955).

The desired Compound (2-1) prepared as mentioned above may be subjected to usual post-treatment such as extraction, concentration, filtration, etc., after the reaction, and, if necessary, may be subjected to purification by the known methods such as recrystallization, various kinds of chromatographies, etc.

(Synthetic method 7)

Synthetic method 7 is a method of obtaining Compound (2-2) (a compound in which $R^1$ in Compound (2) is an acyloxy group having 2 to 4 carbon atoms) by reacting Compound (2-1) and Compound (6) in a solvent in the presence of a base.

As a kind of the solvent, there may be mentioned an ether, a ketone, an amide such as N,N-dimethylacetamide; 1,3-dimethyl-2-imidazolidone, sulforane, dimethylsulfoxide; and a mixture of the above-mentioned solvents; and preferably N,N-dimethylformamide of the amide.

An amount of the solvent may be set in such an amount that Compound (2-1) becomes 5 to 80% by weight; preferably 10 to 70% by weight.

As a kind of the base, it is not specifically limited, and there may be mentioned an organic and inorganic base, for example, organic bases including a tertiary amine such as triethylamine, and DBU; and inorganic bases such as a hydride, hydroxide, carbonate, hydrogen carbonate of an alkali metal or an alkaline earth metal, etc.; preferably potassium carbonate of the inorganic base.

An amount of the base to be used is 1- to 5-fold mol based on the amount of Compound (2-1); preferably 2- to 5-fold mol.

A reaction temperature is not specifically limited and is within the temperature range of room temperature to a boiling point or less of the solvent to be used; preferably 50 to 100° C.

A reaction time may vary depending on the above-mentioned concentration and temperature; and is 0.5 to 8 hours.

As Compound (6), a commercially available product may be used.

The desired Compound (2-2) prepared as mentioned above may be subjected to usual post-treatment such as extraction, concentration, filtration, etc., after the reaction, and, if necessary, may be subjected to purification by the known methods such as recrystallization, various kinds of chromatographies, etc.

(Synthetic method 8)

Synthetic method 8 is a method of obtaining Compound (2-3) by reacting Compound (2-2) and Compound (7) in a solvent.

As a kind of the solvent, there may be mentioned an alcohol such as methanol, ethanol, propanol, butanol, etc.; a nitrile such as acetonitrile, propionitrile, etc.; a ketone such as acetone, methyl ethyl ketone, etc.; an aprotic polar solvent such as N,N-dimethylformamide, dimethylsulfoxide, sulforane, N,N-dimethylimidazolidinone, N-methylpyrrolidone, etc.; water; and a mixture of the above-mentioned solvents; and preferably a mixture of an alcohol (methanol, ethanol) and water.

An amount of the solvent may be set in such an amount that Compound (2-2) becomes 5 to 80% by weight; preferably 10 to 70% by weight.

As Compound (7), there may be mentioned an inorganic base such as sodium hydroxide and potassium hydroxide; preferably sodium hydroxide.

An amount of Compound (7) to be used is 1 to 2-fold mol based on the amount of Compound (2-2), preferably 1 to 1.5-fold mol.

A reaction temperature is within the temperature range of 0° C. to a boiling point or less of the solvent to be used; preferably room temperature to 50° C.

A reaction time may vary depending on the above-mentioned concentration and temperature; and is 0.5 to 3 hours.

The desired Compound (2-3) prepared as mentioned above may be subjected to usual post-treatment such as extraction, concentration, filtration, etc., after the reaction, and, if necessary, may be subjected to purification by the known methods such as recrystallization, various kinds of chromatographies, etc.

(Synthetic method 9)

Synthetic method 9 is a method of obtaining Compound (2-4) by reacting Compound (2-3) and Compound (8) in a solvent or without solvent.

As a kind of the solvent, there may be mentioned a chlorinated or not chlorinated aromatic, aliphatic or alicyclic hydrocarbon, and an ether; and preferably dichloromethane which is a chlorinated aliphatic hydrocarbon.

An amount of the solvent may be set in such an amount that Compound (2-3) becomes 5 to 80% by weight; preferably 10 to 70% by weight.

A reaction temperature is not specifically limited and is within the temperature range of 0° C. to a boiling point or less of the solvent to be used; preferably 0° C. to room temperature.

A reaction time may vary depending on the above-mentioned concentration and temperature; and is 0.5 to 1 hour.

As Compound (8), it is not specifically limited; and preferably diethylaminosulfur trifluoride (DAST) which is a commercially available product as mentioned above.

An amount of Compound (8) to be used is 1 to 2-fold mol based on the amount of Compound (2-3), preferably 1 to 1.5-fold mol.

The desired Compound (2-4) prepared as mentioned above may be subjected to usual post-treatment such as extraction, concentration, filtration, etc., after the reaction, and, if necessary, may be subjected to purification by the known methods such as recrystallization, various kinds of chromatographies, etc.

(Prevention effects)

As the agricultural and horticultural noxious organisms on which a controlling effect by the compound (I) of the present invention can be observed, there may be mentioned agricultural and horticultural noxious insects (e.g. Hemiptera (planthoppers, leafhoppers, aphides, whiteflies, etc.), Lepidoptera (cabbage armyworms, diamond-back moth, leafroller moths, pyralid moths, common cabbage worm, etc.), Coleoptera (Tenebrionid beetles, leafbeetles, weevils, scarabs, etc.), Acarina (citrus red mite, two-spotted spider mite, etc. of Tetranychidae family, pink citrus rust mite of Eriophyidae family, etc.)), nematodes (e.g. root knot nematodes, cystcid nematodes, root lesion nematodes, white-tip nematodes, pine wood nematodes), bulb mite in soil, hygienically noxious insects (e.g. flies, mosquitoes, cockroaches, etc.), noxious insects of stored grains (e.g. rust-red flour beetles, bean weevils, etc..), wood insects (e.g. termite such as formosan subterranean termite, *Reticulitermes speratus* and *Cryptotermes domesticus*; powderpost beetles, drugstore beetles, carpenter moths, long-horned beetle, bark beetles, etc.) and also agricultural and horticultural diseases (e.g. wheat brown rust, barley powdery mildew, cucumber downy mildew, rice blast, tomato late blight, etc.).

(Agricultural and horticultural fungicide)

The agricultural and horticultural fungicide of the present invention has particularly remarkable in insecticidal, acaricidal and nematocidal effects, and contains one kind or more of Compound (1) as an effective ingredient.

Compound (1) may be used singly, but usually, it is preferred to formulate a carrier, surfactant, dispersant, auxiliary, etc. (for example, it is prepared as a composition such as dust powder, an emulsifiable concentrate, a fine granule, a granule, a wettable powder, an oily suspension, an aerosol, etc.) according to the conventionally known method.

As the carrier, there may be mentioned, for example, a solid carrier such as bentonite, clay, kaolin, diatomaceous earth, white carbon, vermiculite, calcium hydroxide, siliceous sand, ammonium sulfate, urea, etc., a liquid carrier such as hydrocarbon (kerosine, mineral oil, etc.), aromatic hydrocarbon, (benzene, toluene, xylene, etc.), chlorinated hydrocarbon (chloroform, carbon tetrachloride, etc.), ethers (dioxane, tetrahydrofuran, etc.), ketones (acetone, cyclohexanone, isophorone, etc.), esters (ethyl acetate, ethyleneglycol acetate, dibutyl maleate, etc.), alcohols (methanol, n-hexanone, ethylene glycol, etc.), polar solvent (dimethylformamide, dimethylsulfoxide, etc.), water, etc.; a gas carrier such as air, nitrogen, a carbonic acid gas, fleone, etc. (in this case, mixture spreading can be carried out), and the like.

As the surfactant and dispersant which can be used for improving attachment of the present chemical to and absorption thereof in animals and plants, and improving characteristics such as dispersion, emulsification and spreading of the chemical, there may be mentioned, for example, alcohol sulfates, alkylsulfonate, lignosulfonate and polyoxyethylene glycol ether. Further, for improving properties of its formulation, for example, carboxymethyl cellulose, polyethylene glycol and gum arabic can be used as an auxiliary.

In preparation of the present chemical, the above carrier, surfactant, dispersant and auxiliary can be used singly or in a suitable combination, respectively, depending on the respective purposes.

When the compound (I) of the present invention is made into formulations, the concentration of the active ingredient is generally 1 to 50% by weight in an emulsifiable concentrate, generally 0.3 to 25% by weight in a dustable powder, generally 1 to 90% by weight in a wettable powder, generally 0.5 to 5% by weight in a granule, generally 0.5 to 5% by weight in an oily suspension, and generally 0.1 to 5% by weight in an aerosol.

These formulations can be provided for various uses by diluting them to have a suitable concentration and spraying them to stems and leaves of plants, soil and paddy field surface, or by applying them directly thereto, depending on the purposes.

EXAMPLES

In the following, the present invention will be specifically explained by referring to Reference example and Examples. Incidentally, these will not limit the scope of the present invention.

Reference Example 1 (Synthetic method of Compound (4) and Compound (11))

(1) Synthesis of 6-ethyl-4-hydroxy-5-iodopyrimidine (Compound (11))

Iodine (50.8 g) was added to acetic acid (700 ml), chlorine (15 g) was blown thereinto, and acetic acid (150 ml) solution of 6-ethyl-4-hydroxypyrimidine (50 g) was added dropwise to the solution and the mixture was stirred for 4 hours.

After completion of the reaction, acetic acid was distilled off under reduced pressure, the obtained crystal was purified by recrystallization from ethyl acetate to obtain 24.8 g of the desired compound as colorless crystal.
m.p. 192–193° C.
$^1$H-NMR (CDCl$_3$, δ ppm)
1.22–1.25 (3H, q), 2.84–2.90 (2H, q), 7.98(1H, s), 9.74–11.24 (1H, bs)

(2) Synthesis of 4-chloro-6-ethyl-5-iodopyrimidine (Compound (4))

To 6-ethyl-4-hydroxy-5-iodopyrimidine (10 g) was added phosphorous oxychloride (40 g) and the mixture was refluxed under heating for 4 hours.

After completion of the reaction, excess phosphorous oxychloride was distilled off under reduced pressure, the obtained residue was poured into ice water, and the desired compound was extracted with toluene. The extract was washed with water and dried over anhydrous sodium sulfate, and the solvent was distilled off under reduced pressure.

The obtained oily product was purified by silica gel column (Wako gel C-200, eluted by toluene:ethyl acetate= 10:1) to obtain 9.3 g of the desired compound as pale yellowish crystal.
m.p. 48–50° C.
$^1$H-NMR (CDCl$_3$, δ ppm)
1.28–1.34 (3H, t), 3.02–3.09 (1H, q), 8.78 (1H, s)

Example 1

Synthetic method of Compound (2)

(1) Synthesis of 4-chloro-6-(1-chloroethyl)-5-iodopyrimidine (Compound 2-(1))

In chloroform (100 ml) was dissolved 4-chloro-6-ethyl-iodopyrimidine (5 g), and chlorine gas was blown into the solution while stirring at room temperature.

After completion of the reaction, nitrogen gas was blown into the mixture to remove excess chlorine gas, and the solvent was distilled off under reduced pressure.

The obtained oily product was purified by silica gel column (Wako gel C-200, eluted by toluene:ethyl acetate= 20:1) to obtain 3.4 g of the desired compound as pale yellowish oily liquid.
$^1$H-NMR (CDCl$_3$, δ ppm)
1.87–1.90 (3H, d), 5.44–5.51 (1H, q), 8.86 (1H, s)

(2) Synthesis of 4-chloro-6-(1-fluoroethyl)-5-iodopyrimidine (Compound 2-(3))

In dichloromethane (20 ml) was dissolved 4-chloro-6-(1-hydroxyethyl)-5-iodopyrimidine (0.5 g), diethylaminosulfur trifluoride (0.3 g) was added dropwise to the solution under ice-cooling while stirring, and the mixture was stirred for additional one hour at room temperature to complete the reaction.

Cold water was added to the reaction mixture, the dichloromethane layer was separated, washed with water, and dried over anhydrous sodium sulfate. Then, the solvent was distilled off under reduced pressure, and the obtained residue was purified by column chromatography (Wako gel C-200, eluted by chloroform) to obtain 0.4 g of the desired compound as pale yellowish liquid.
$^1$H-NMR (CDCl$_3$, δ ppm)
1.63–1.77 (3H, d-d), 5.88–6.08 (1H, d-q), 8.70 (1H, s)

(3) Synthesis of 6-(1-acetoxyethyl)-4-chloro-5-iodopyrimidine (Compound 2-(4))

In N,N-dimethylformamide (70 ml) was dissolved 4-chloro-6-(1-chloroethyl)-5-iodopyrimidine (3.6 g), potassium acetate (2.4 g) and potassium carbonate (0.7 g) were added to the solution and the mixture was heated at about 60° C. for 4 hours while stirring.

After completion of the reaction, water was added to the reaction mixture, the oily product separated was extracted with toluene and the extract was washed with water and dried over anhydrous sodium sulfate. Then, the solvent was distilled off under reduced pressure, and the obtained residue was purified by column chromatography (Wako gel C-200, eluted by toluene:ethyl acetate=10:1) to obtain 1.0 g of the desired compound as colorless crystal.
m.p. 55–58° C.
$^1$H-NMR (CDCl$_3$, δ ppm)
1.57–1.60 (3H, d), 2.14 (3H, s), 5.99–6.09 (1H, q), 8.83 (1H, s)

(4) Synthesis of 4-chloro-6-(1-hydroxyethyl)-5-iodopyrimidine (Compound 2-(6))

In ethanol (20 ml) was dissolved 6-(1-acetoxyethyl)-4-chloro-5-iodopyrimidine (1.0 g), and 1N sodium hydroxide aqueous solution (20 ml) was added dropwise to the solution while stirring. After the dropping addition, the mixture was stirred for additional one hour at room temperature to complete the reaction. Then, the solvent was distilled off under reduced pressure, and the desired compound was extracted with ethyl acetate. The extract was washed with water and dried over anhydrous sodium sulfate, and the solvent was distilled off under reduced pressure.

The obtained residue was purified by column chromatography (Wako gel C-200, eluted by toluene:ethyl acetate= 20:1) to obtain 0.5 g of the desired compound as pale yellowish liquid.

¹H-NMR (CDCl₃, δ ppm)
1.43–1.46 (3H, d), 4.13–4.16 (1H, m), 5.09–5.17 (1H, q), 8.64 (1H, s)

(5) Syntheses of other compounds (2) in Table 1

In accordance with the methods described in the above (1) to (4), other compounds (2) shown in Table 1 were synthesized.

The compounds (2) thus synthesized as mentioned above and the properties thereof are shown in Table 1.

TABLE 1

(2)

[Chemical structure: pyrimidine with Cl, I substituents and CH(R¹)* group]

| Compound | R¹ | Property |
|---|---|---|
| 2-(1) | Cl | $N_D^{20.0} 1.6156$ |
| 2-(2) | Br | pale brown liquid$^{(note)}$ |
| 2-(3) | F | $N_D^{19.5} 1.5204$ |
| 2-(4) | —OCOCH₃ | m.p. 55–58° C. |
| 2-(5) | —OCOC₂H₅ | |
| 2-(6) | OH | $N_D^{19.6} 1.5242$ |

(Note)
¹H-NMR (CDCl₃, δ ppm)
2.06–2.08 (3H, d), 5.43–5.51 (1H, q), 8.84 (1H, s)

Example 2

Synthetic method of Compound (1)

(1) Synthesis of 6-(1-fluoroethyl)-5-iodo-4-(2-phenylethylamino)pyrimidine (Compound 1-(1))

In 20 ml of toluene were dissolved 2-phenylethylamine (0.6 g) and triethylamine (0.6 g), then, 4-chloro-6-(1-fluoro-ethyl)-5-iodopyrimidine (1.5 g) was added to the solution, and the mixture was heated at about 60° C. for 3 hours while stirring.

After completion of the reaction, the solvent was distilled off under reduced pressure and the obtained residue was purified by silica gel column chromatography (Wako gel C-200, eluted by toluene:ethyl acetate=10:1) to obtain 1.1 g of the desired compound as pale yellowish crystal.
¹H-NMR (CDCl₃, δ ppm)
1.58–1.71 (3H, d-d), 2.92–2.97 (2H, t), 3.74–3.81 (2H, q), 5.68–5.73 (1H, m), 5.73–5.95 (1H, d-q), 7.18–7.35 (5H, m), 8.48 (1H, s)

(2) Synthesis of 6-(1-chloroethyl)-5-iodo-4-(2-phenylethylamino)pyrimidine (Compound 1-(2))

In 20 ml of toluene were dissolved 2-phenylethylamine (0.6 g) and triethylamine (0.6 g), then, 4-chloro-6-(1-chloro-ethyl)-5-iodopyrimidine (1.5 g) was added to the solution, and the mixture was heated at about 60° C. for 3 hours while stirring.

After completion of the reaction, the solvent was distilled off under reduced pressure, and the obtained residue was purified by silica gel column chromatography (Wako gel C-200, eluted by toluene:ethyl acetate=10:1) to obtain 1.2 g of the desired compound as colorless crystal.
¹H-NMR (CDCl₃, δ ppm)
1.82–1.85 (3H, d), 2.92–2.97 (2H, t), 3.73–3.83 (2H, m), 5.28–5.35 (1H, q), 5.41–5.61 (1H, m), 7.23–7.37 (5H, m), 8.46 (1H, s)

(3) Synthesis of 6-(1-acetoxyethyl)-5-iodo-4-(2-phenylethylamino)pyrimidine (Compound 1-(3))

In 20 ml of toluene were dissolved 2-phenylethylamine (0.6 g) and triethylamine (0.6 g), then, 4-chloro-6-(1-acetoxy-ethyl)-5-iodopyrimidine (1.7 g) was added to the solution, and the mixture was heated at about 60° C. for 3 hours while stirring.

After completion of the reaction, the solvent was distilled off under reduced pressure and the obtained residue was purified by silica gel column chromatography (Wako gel C-200, eluted by toluene:ethyl acetate=10:1) to obtain 1.2 g of the desired compound as pale yellowish liquid.
¹H-NMR (CDCl₃, δ ppm)
1.50–1.54 (3H, d), 2.12 (3H, s), 2.92–2.99 (2H, m), 3.74–3.82 (2H, m), 5.54–5.70 (1H, m), 5.82–5.91 (1H, q), 7.26–7.34 (5H, m), 8.55 (1H, s)

(4) Synthesis of 6-(1-hydroxyethyl)-5-iodo-4-(2-phenylethylamino)pyrimidine (Compound 1-(4))

In 20 ml of toluene were dissolved 2-phenylethylamine (0.6 g) and triethylamine (0.6 g), then, 4-chloro-6-(1-hydroxy-ethyl)-5-iodopyrimidine (1.4 g) was added to the solution, and the mixture was heated at about 60° C. for 3 hours while stirring.

After completion of the reaction, the solvent was distilled off under reduced pressure and the obtained residue was purified by silica gel column chromatography (Wako gel C-200, eluted by toluene:ethyl acetate=5:1) to obtain 1.0 g of the desired compound as pale yellowish viscous liquid.
¹H-NMR (CDCl₃, δ ppm)
1.39–1.44 (3H, d), 2.92–2.97 (2H, t), 3.73–3.84 (2H, m), 4.13–4.20 (1H, m), 4.81–4.87 (1H, q), 5.41–5.58 (1H, m), 7.22–7.37 (2H, m), 8.40 (1H, s)

(5) Synthesis of 6-(1-fluoroethyl)-5-iodo-4-[2-(4-fluorophenyl)ethylamino]pyrimidine (Compound 1-(5))

In N,N-dimethylformamide (30 ml) was dissolved 6-(1-bromoethyl)-5-iodo-4-[2-(4-fluorophenyl)ethylamino]pyrimidine (2.0 g), cesium fluoride (1.5 g) was added to the solution, and the mixture was heated at 120–130° C. for 12 hours while stirring.

After completion of the reaction, water was added to the solution, and the desired product was extracted with ethyl acetate. The extract was washed with water and dried over anhydrous sodium sulfate, and the solvent was distilled off under reduced pressure. The obtained residue was purified by silica gel column chromatography (Wako gel C-200, eluted by toluene:ethyl acetate=10:1) to obtain 1.3 g of the desired compound as colorless crystal.
¹H-NMR (CDCl₃, δ ppm)
1.59–1.72 (3H, d-d), 2.82–2.94 (2H, t), 3.71–3.79 (2H, m), 5.41–5.68 (1H, m), 5.68–5.91 (1H, d-q), 6.898–7.05 (2H, m), 7.16–7.22 (2H, m), 8.48 (1H, s)

(6) Synthesis of 6-(1-bromoethyl)-5-iodo-4-[2-(4-trifluoromethoxyphenyl)ethylamino]pyrimidine (Compound 1-(19))

In toluene (50 ml) were dissolved 2-(4-trifluoromethoxyphenyl)ethylamine (1.0 g) and triethylamine (1.0 g) then, 4-chloro-6-(1-bromoethyl)-5-iodopyrimidine (1.8 g) was added to the solution, and the mixture was heated at about 60° C. for 3 hours while stirring.

After completion of the reaction, the solvent was distilled off under reduced pressure and the obtained residue was purified by silica gel column chromatography (Wako gel C-200, eluted by toluene:ethyl acetate=10:1) to obtain 1.6 g of the desired compound as pale yellowish liquid.
¹H-NMR (CDCl₃, δ ppm)
1.81–1.84 (3H, d), 2.92–2.97 (2H, t), 3.72–3.79 (2H, q), 5.30–5.37 (1H, m), 5.50–5.72 (1H, m), 7.17–7.27 (4H, m), 8.46 (1H, s)

(7) Synthesis of 6-(1-chloroethyl)-5-iodo-4-[2-(4-trifluoromethoxyphenyl)ethylamino]pyrimidine (Compound 1- (20))

In toluene (50 ml) were dissolved 2-(4-trifluoromethoxyphenyl)ethylamine (1.0 g) and triethylamine (1.0 g), then, 4-chloro-6-(1-chloroethyl)-5-iodopyrimidine (1.5 g) was added to the solution, and the mixture was heated at about 60° C. for 3 hours while stirring.

After completion of the reaction, the solvent was distilled off under reduced pressure and the obtained residue was purified by silica gel column chromatography (Wako gel C-200, eluted by toluene:ethyl acetate=10:1) to obtain 1.3 g of the desired compound as pale yellowish liquid.

$^1$H-NMR (CDCl$_3$, δ ppm)
1.81–1.84 (3H, d), 2.92–2.97 (2H, t), 3.72–3.80 (2H, q), 5.28–5.35 (1H, q), 5.56–5.73 (1H, m), 7.17–7.27 (4H, m), 8.47 (1H, s)

(8) Synthesis of 6-(1-acetoxyethyl)-5-iodo-4-[2-(4-trifluoromethoxyphenyl)ethylamino]pyrimidine (Compound 1- (21))

In DMF (50 ml) was dissolved 6-(1-chloroethyl)-5-iodo-4-[2-(4-trifluoromethoxyphenyl)ethylamino]pyrimidine (1.3 g), then, potassium acetate (1.6 g) and potassium carbonate (1.1 g) were added to the solution, and the mixture was heated at about 60° C. for 3 hours while stirring.

After completion of the reaction, water was added to the reaction mixture and the separated oily product was extracted with ethyl acetate. The extract was washed with water and dried over anhydrous sodium sulfate, and the solvent was distilled off under reduced pressure. The obtained residue was purified by silica gel column chromatography (Wako gel C-200, eluted by toluene:ethyl acetate=10:1) to obtain 1.0 g of the desired compound as colorless powdery crystal.

$^1$H-NMR (CDCl$_3$, δ ppm)
1.50–1.53 (3H, d), 2.16 (3H, s), 2.91–2.95 (2H, t), 3.70–3.79 (2H, q), 5.50–5.65 (1H, m), 5.84–5.91 (1H, q), 7.16–7.27 (4H, m), 8.42 (1H, s)

(9) Synthesis of 6-(1-hydroxyethyl)-5-iodo-4-[2-(4-trifluoromethoxyphenyl)ethylamino]pyrimidine (Compound 1-(22))

In ethanol (20 ml) was dissolved 6-(1-acetoxyethyl)-5-iodo-4-[2-(4-trifluoromethoxyphenyl)ethylamino]pyrimidine (1.0 g), then, 1N sodium hydroxide aqueous solution (20 ml) was added to the solution, and stirred for one hour at room temperature.

After completion of the reaction, water was added to the reaction mixture and the separated oily product was extracted with ethyl acetate. The extract was washed with water and dried over anhydrous sodium sulfate, the solvent was distilled off under reduced pressure. The obtained residue was purified by silica gel column chromatography (Wako gel C-200, eluted by toluene:ethyl acetate=1:1) to obtain 0.9 g of the desired compound as pale yellowish liquid.

$^1$H-NMR (CDCl$_3$, δ ppm)
1.40–1.45 (3H, d), 2.93–2.98 (2H, t), 3.73–3.82 (2H, q), 4.08–4.16 (1H, m), 4.82–4.89 (1H, q), 5.48–5.68 (1H, m), 7.17–7.30 (4H, m), 8.40 (1H, s)

(10) Synthesis of 6-(1-fluoroethyl)-5-iodo-4-[2-(4-trifluoromethoxyphenyl)ethylamino]pyrimidine (Compound 1- (23))

In dichloromethane (20 ml) was dissolved 6-(1-hydroxyethyl)-5-iodo-4-[2-(4-trifluoromethoxyphenyl)ethylamino]pyrimidine (0.9 g), diethylaminosulfur trifluoride (0.3 g) was added dropwise to the solution under cooling while stirring, and it was stirred for additional one hour at room temperature.

After completion of the reaction, water was added to the reaction mixture and the chloromethane layer was collected by separation. The chloromethane layer was washed with water and dried over anhydrous sodium sulfate. Then, the solvent was distilled off under reduced pressure. The obtained residue was purified by silica gel column chromatography (Wako gel C-200, eluted by toluene:ethyl acetate= 1:1) to obtain 0.6 g of the desired compound as colorless powdery crystal.

$^1$H-NMR (CDCl$_3$, δ ppm)
1.61–1.70 (3H, d-d), 2.92–2.98 (2H, t), 3.73–3.81 (2H, m), 5.62–5.66 (1H, m), 5.66–5.91 (1H, d-q), 7.16–7.28 (4H, m), 8.48 (1H, s)

(11) Syntheses of other compounds (1) in Table 2

In accordance with the methods described in the above-mentioned (1) to (10), other compounds (1) shown in Table 2 were synthesized.

The compounds (1) thus synthesized as mentioned above and the properties thereof are shown in Table 2.

TABLE 2

(1)

| Compound | R$^1$ | (R$^2$)$_n$ | Property |
|---|---|---|---|
| 1-(1) | F | H | m.p. 78–80° C. |
| 1-(2) | Cl | H | m.p. 101–102° C. |
| 1-(3) | CH$_3$COO— | H | N$_D^{18.9}$1.4934 |
| 1-(4) | OH | H | viscous |
| 1-(5) | F | 4-F | m.p. 89–91° C. |
| 1-(6) | Cl | 4-F | m.p. 81–83° C. |
| 1-(7) | CH$_3$COO— | 4-F | N$_D^{18.9}$1.5294 |
| 1-(8) | OH | 4-F | N$_D^{21.4}$1.5754 |
| 1-(9) | F | 4-Cl | m.p. 88–92° C. |
| 1-(10) | Cl | 4-Cl | N$_D^{21.8}$1.5956 |
| 1-(11) | CH$_3$COO— | 4-Cl | N$_D^{21.5}$1.5416 |
| 1-(12) | OH | 4-Cl | viscous |
| 1-(13) | F | 4-CH$_3$ | m.p. 63–66° C. |
| 1-(14) | Cl | 4-CH$_3$ | N$_D^{20.7}$1.5970 |
| 1-(15) | CH$_3$COO— | 4-CH$_3$ | N$_D^{20.0}$1.5120 |
| 1-(16) | OH | 4-CH$_3$ | viscous |
| 1-(17) | F | 3-CH$_3$O | m.p. 95–96° C. |
| 1-(18) | F | 3-Cl, 4-Cl | |
| 1-(19) | Br | 4-CF$_3$O | viscous |
| 1-(20) | Cl | 4-CF$_3$O | N$_D^{20.2}$1.5392 |
| 1-(21) | CH$_3$COO— | 4-CF$_3$O | m.p. 77–79° C. |
| 1-(22) | OH | 4-CF$_3$O | N$_D^{23.7}$1.5202 |
| 1-(23) | F | 4-CF$_3$O | m.p. 71–72° C. |
| 1-(24) | F | 4-CF$_3$CH$_2$O | |
| 1-(25) | OH | 4-CF$_3$CH$_2$O | |
| 1-(26) | F | 4-C$_2$H$_5$O | |
| 1-(27) | F | 4-CF$_3$ | |
| 1-(28) | C$_2$H$_5$COO— | 4-CF$_3$ | |
| 1-(29) | F | 4-CHF$_2$O | |
| 1-(30) | OH | 4-CHF$_2$O | |

Example 3

Preparation of formulations (1) Preparation of granule

Five parts by weight of Compound (1) were uniformly mixed with 35 parts by weight of bentonite, 57 parts by weight of talc, 1 part by weight of Neopelex powder (trade name, produced by Kao K.K.) and 2 parts by weight of sodium lignosulfonate, then the mixture was kneaded with addition of a small amount of water, followed by granulation and drying, to obtain a granule.

(2) Preparation of wettable powder

Ten parts by weight of Compound (1) were uniformly mixed with 70 parts by weight of kaolin, 18 parts by weight of white carbon, 1.5 parts by weight of Neopelex powder (trade name, produced by Kao K.K.) and 0.5 part by weight of Demol (trade name, produced by Kao K.K.), then the mixture was pulverized to obtain a wettable powder.

(3) Preparation of emulsifiable concentrate

Twenty parts by weight of Compound (1) were uniformly mixed with 70 parts by weight of xylene by adding 10 parts by weight of Toxanone (trade name, produced by Sanyo Kasei Kogyo), and dissolved therein to obtain an emulsifiable concentrate.

(4) Preparation of dustable powder

Five parts by weight of Compound (1) powder were uniformly mixed with 50 parts by weight of talc and 45 parts by weight of kaolin to obtain dustable powder.

Example 4

Tests of effects (1) Test of effect on southern root knot nematodes

The respective wettable powders of Compounds (1) shown in Table 2 prepared as in Example 3 were diluted to 300 ppm with water, 0.1 ml of which is taken into the test tubes, and 0.9 ml of a solution containing 500 southern potato root knot nematodes was added thereto, respectively.

Subsequently, these test tubes were left to stand in a thermostat chamber at 25° C., and after 2 days, nematodecidal rate was determined by observing with microscope.

As a result, Compounds 1-(1), 1-(5), 1-(9), 1-(13), 1-(17) and 1-(23) showed the nematodecidal effect of 100%.

(2) Test of effect on two-spotted spider mite

The respective wettable powders of Compounds (1) shown in Table 2 prepared as in Example 3 were diluted to 300 ppm with water containing a surfactant (0.01%). In these respective solutions, kidney bean leaves (diameter: 20 mm) on which 15 two-spotted spider mite female adults were parasitized for 24 hours to bear eggs thereon and removed were dipped for 10 seconds, respectively.

Subsequently, these leaves were left to stand in a thermostat chamber at 25° C., and after 3 days, acaricidal rate was determined by counting living and dead insects in the respective leaves.

As a result, Compounds 1-(1), 1-(5), 1-(9), 1-(13), 1-(17) and 1-(23) showed the acaricidal effect of 80% or more.

(3) Test of effect on diamondback moth

The respective wettable powders of Compounds (1) shown in Table 2 prepared as in Example 3 were diluted to 300 ppm with water containing a surfactant (0.01%), and in these respective chemical solutions, cabbage leaves (5×5 cm) were dipped for 30 seconds, and each leaf was put into the respective plastic cups and air-dried.

Subsequently, 10 diamondback moths (3rd instar larvae) were placed in the respective cups, and put the lids on them and they were left to stand in a thermostat chamber at 25° C., and after 2 days, insecticidal rate was determined by counting living and dead insects in the respective cups.

As a result, Compounds 1-(1), 1-(3), 1-(5), 1-(9), 1-(13), 1-(17) and 1-(23) showed the insecticidal effect of 100%.

(4) Test of effect on brown rice planthopper

The respective wettable powders of Compounds (1) shown in Table 2 prepared as in Example 3 were diluted to 300 ppm with water containing a surfactant (0.01%), and in these respective chemical solutions, young seedlings of rice were dipped for 30 seconds, and after air-drying, each was put into the respective glass cylinders.

Subsequently, 10 brown rice planthoppers (4th instar larvae) were placed in the respective glass cylinders, and porous stoppers were each placed on them and they were left to stand in a thermostat chamber at 25° C., and after 4 days, insecticidal rate was determined by counting living and dead insects in the respective cylinders.

As a result, Compounds 1-(1), 1-(5), 1-(9), 1-(13), 1-(17) and 1-(23) showed the insecticidal effect of 100%.

(5) Test of effect on green rice leafhopper

The respective wettable powders of Compounds (1) shown in Table 2 prepared as in Example 3 were diluted to 300 ppm with water containing a surfactant (0.01%), and in these respective chemical solutions, young seedlings of rice were dipped for 30 seconds, and after air-drying, each was put into the respective glass cylinders.

Subsequently, 10 green rice leafhoppers (4th instar larvae) were placed in the respective glass cylinders, and porous stoppers were each placed on them and they were left to stand in a thermostat chamber at 25° C., and after 4 days, insecticidal rate was determined by counting living and dead insects in the respective cylinders.

As a result, Compounds 1-(1), 1-(5), 1-(9), 1-(13), 1-(17) and 1-(23) showed the insecticidal effect of 100%.

(6) Test of effect on tobacco cutworm

The respective wettable powders of Compounds (1) shown in Table 2 prepared as in Example 3 were diluted to 500 ppm with water containing a surfactant (0.01%), and in these respective chemical solutions, leave of soybean were dipped for 30 seconds. After air-drying, each of the leave was put into the respective plastic cups, 10 tobacco cutworm (2nd instar larvae) were placed in the respective cups, and put the lids on them and they were left to stand in a thermostat chamber at 25° C. After 2 days, insecticidal rate was determined by counting living and dead insects in the respective cups.

As a result, Compounds 1-(5), 1-(9) and 1-(23) showed the insecticidal effect of 100%.

(7) Test of effect on wheat brown rust (Prevention effect)

In plastic flower pots having a diameter of 6 cm, 10 wheats (variety: Kobushi Komugi) were grown per one flowerpot, and to young plants at 1.5 leaf stage, the wettable powder of Compounds (1) shown in Table 2 prepared as in Example 3 were diluted to 500 ppm with water containing a surfactant (0.01%), and sprayed it in an amount of 20 ml per one flowerpot, respectively.

After spraying, they were cultivated in a glass greenhouse for 2 days, then spore suspension of wheat brown rust bacteria ($7 \times 10^4$ spore/ml) was sprayed uniformly to the plants to be inoculated thereinto.

After inoculation, they were kept in a glass greenhouse for one week, and the degree of lesion of wheat brown rust appeared on the first leaves was examined.

As a result, Compounds 1-(1), 1-(5), 1-(9), 1-(13), 1-(17), 1-(20) and 1-(23) showed area of lesionas 20% or less.

Industrial applicability

The novel 5-iodo-4-phenethylaminopyrimidine derivative of the present invention is useful as agricultural and horticultural pesticides.

Further, the novel 4-chloro-5-iodo-6-(α-substituted ethyl) pyrimidine of the present invention is useful as an intermediate for medicaments or agricultural chemicals.

What is claimed is:

1. A 5-iodo-4-phenethylaminopyrimidine derivative represented by the following formula (1):

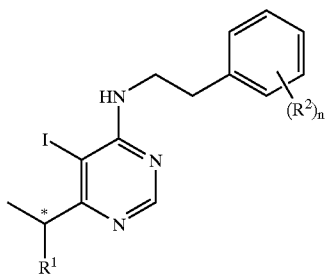

wherein $R^1$ represents a halogen atom, an acyloxy group having 2 to 4 carbon atoms or a hydroxyl group; $R^2$ represents a hydrogen atom, a halogen atom, an alkyl group having 1 to 4 carbon atoms, a haloalkyl group having 1 to 4 carbon atoms, an alkoxy group having 1 to 4 carbon atoms, or a haloalkoxy group having 1 to 4 carbon atoms; n is an integer of 1 to 3; and * represents an asymmetric carbon atom.

2. The 5-iodo-4-phenethylaminopyrimidine derivative according to claim 1, wherein $R^1$ represents a chlorine atom, a fluorine atom, an acetyloxy group or a hydroxyl group, $R^2$ represents a hydrogen atom, a chlorine atom, a fluorine atom, a methyl group, a trifluoromethyl group, a methoxy group, a trifluoromethoxy group or a 2,2,2-trifluoroethoxy group and n is an integer of 1 or 2.

3. The 5-iodo-4-phenethylaminopyrimidine derivative according to claim 1, wherein the compound represented by the formula (1) is selected from the group consisting of:
   (1) Compound (1) in which $R^1$ is a halogen atom and $R^2$ is a hydrogen atom,
   (2) Compound (1) in which $R^1$ and $R^2$ are halogen atoms and n is 1,
   (3) Compound (1) in which $R^1$ is an acyloxy group having 2 to 4 carbon atoms and $R^2$ is a hydrogen atom,
   (4) Compound (1) in which $R^1$ is a halogen atom, $R^2$ is an alkyl group having 1 to 4 carbon atoms and n is 1,
   (5) Compound (1) in which $R^1$ is a halogen atom, $R^2$ is an alkoxy group having 1 to 4 carbon atoms and n is 1, and
   (6) Compound (1) in which $R^1$ is a halogen atom, $R^2$ is a haloalkoxy group having 1 to 4 carbon atoms and n is 1.

4. The 5-iodo-4-phenethylaminopyrimidine derivative according to claim 1, wherein the compound represented by the formula (1) is selected from the group consisting of:
   6-(1-fluoroethyl)-5-iodo-4-(2-phenylethylamino)pyrimidine,
   6-(1-chloroethyl)-5-iodo-4-(2-phenylethylamino)pyrimidine,
   6-(1-acetoxyethyl)-5-iodo-4-(2-phenylethylamino)pyrimidine,
   6-(1-hydroxyethyl)-5-iodo-4-(2-phenylethylamino)pyrimidine,
   6-(1-fluoroethyl)-5-iodo-4-[2-(4-fluorophenyl)ethylamino]pyrimidine,
   6-(1-bromoethyl)-5-iodo-4-[2-(4-trifluoromethoxyphenyl)ethylamino]pyrimidine,
   6-(1-chloroethyl)-5-iodo-4-[2-(4-trifluoromethoxyphenyl)ethylamino]pyrimidine,
   6-(1-acetoxyethyl)-5-iodo-4-[2-(4-trifluoromethoxyphenyl)ethylamino]pyrimidine,
   6-(1-hydroxyethyl)-5-iodo-4-[2-(4-trifluoromethoxyphenyl)ethylamino]pyrimidine, and
   6-(1-fluoroethyl)-5-iodo-4-[2-(4-trifluoromethoxyphenyl)ethylamino]pyrimidine.

5. A 4-chloro-5-iodo-6-(α-substituted ethyl)pyrimidine represented by the following formula (2):

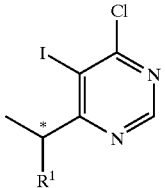

wherein $R^1$ represents a halogen atom, an acyloxy group having 2 to 4 carbon atoms or a hydroxyl group; and * represents an asymmetric carbon atom.

6. The 4-chloro-5-iodo-6-(α-substituted ethyl)pyrimidine according to claim 3, wherein $R^1$ represents a chlorine atom, a fluorine atom, an acetyloxy group or a hydroxyl group.

7. The 4-chloro-5-iodo-6-(α-substituted ethyl)pyrimidine according to claim 5, wherein the compound represented by the formula (2) is selected from the group consisting of:
   4-chloro-6-(1-chloroethyl)-5-iodopyrimidine,
   4-chloro-6-(1-fluoroethyl)-5-iodopyrimidine, and
   6-(1-acetoxyethyl)-4-chloro-5-iodopyrimidine.

8. A process for producing a 4-chloro-5-iodo-6-(α-substituted ethyl)pyrimidine represented by the following formula (2-1):

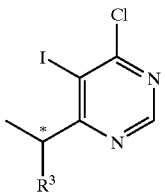

wherein $R^3$ represents a chlorine atom or a bromine atom and * represents an asymmetric carbon atom, which comprises allowing a pyrimidine represented by the following formula (4):

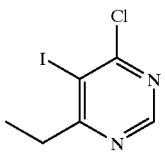

to react with a halogen represented by the following formula (5):

$(R^3)_2$       (5)

wherein $R^3$ has the same meaning as defined above.

9. An agricultural and horticultural pesticide composition comprising the 5-iodo-4-phenethylaminopyrimidine derivative represented by the formula (1) according to claim 1 as an effective ingredient and an agriculturally or horticulturally acceptable carrier.

* * * * *